(12) United States Patent
Wekselman et al.

(10) Patent No.: US 12,678,126 B2
(45) Date of Patent: Jul. 14, 2026

(54) SAFETY ALERT BASED ON 4D INTRACARDIAC ECHO (ICE) CATHETER TRACKING

(71) Applicant: Biosense Webster (Israel) Ltd., Yokneam (IL)

(72) Inventors: Guy Wekselman, Tel Aviv (IL); Nadav Barnea, Haifa (IL); Lior Greenbaum, Zoran (IL); Hadassa Elisheva Hartman, Mitzpe Ilan (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/937,768

(22) Filed: Nov. 5, 2024

(65) Prior Publication Data

US 2025/0204885 A1     Jun. 26, 2025

Related U.S. Application Data

(63) Continuation of application No. 17/901,325, filed on Sep. 1, 2022, now Pat. No. 12,161,506.

(51) Int. Cl.
A61B 5/00 (2006.01)
A61B 8/08 (2006.01)
(Continued)

(52) U.S. Cl.
CPC .......... A61B 8/0841 (2013.01); A61B 8/0883 (2013.01); A61B 8/12 (2013.01);
(Continued)

(58) Field of Classification Search
CPC ....... A61B 8/0841; A61B 8/0993; A61B 8/12; A61B 2017/00119; A61B 2017/00243; A61B 17/00234; A61B 2034/2051
See application file for complete search history.

(56) References Cited

U.S. PATENT DOCUMENTS 6,556,695 B1     4/2003   Packer et al.
7,778,686 B2     8/2010   Vass et al.
(Continued)

FOREIGN PATENT DOCUMENTS

EP          1224621 B1     4/2004
EP          3804630 A1     4/2021
WO     2021/168061 A1     8/2021

OTHER PUBLICATIONS

International Search Report for corresponding PCT Appln. No. PCT/IB2023/057820 dated Oct. 30, 2023.
(Continued)

*Primary Examiner* — Joel F Brutus
(74) *Attorney, Agent, or Firm* — Smith, Gambrell & Russell LLP

(57)     ABSTRACT

A medical system includes an ultrasound probe, a treatment probe, and processor. Ultrasound probe and treatment probe are configured for insertion into an organ, to, respectively, image a volume of the organ, and introduce a treatment device therein. The probes respectively include first sensor configured to output first signals indicative of first positions of an ultrasound transducer array of the probe inside the organ, and second sensor configured to output second signals indicative of second positions of the treatment device inside the organ. The processor is configured to receive tags added to ultrasound images acquired using the ultrasound probe and mark tissue regions of the organ, register first positions of ultrasound transducer array and second positions of treatment device with one another, using registration, track relative position between treatment device and tagged tissue regions, and (iv) alert user when treatment device is within predefined proximity to tagged tissue region.

20 Claims, 2 Drawing Sheets

(51) Int. Cl.

| | | |
|---|---|---|
| *A61B 8/12* | (2006.01) |
| *A61B 17/00* | (2006.01) |
| *A61B 34/20* | (2016.01) |

(52) U.S. Cl.
CPC ........ *A61B 17/00234* (2013.01); *A61B 34/20* (2016.02); *A61B 2017/00119* (2013.01); *A61B 2017/00243* (2013.01); *A61B 2034/2051* (2016.02)

(56) References Cited

U.S. PATENT DOCUMENTS

| | | | |
|---|---|---|---|
| 7,981,038 B2 | 7/2011 | Kanade et al. | |
| 8,989,842 B2 | 3/2015 | Li et al. | |
| 2006/0253032 A1* | 11/2006 | Altmann | A61B 8/4416 |
| | | | 600/466 |
| 2014/0316269 A1* | 10/2014 | Zhang | A61B 8/4209 |
| | | | 602/1 |
| 2015/0112229 A1* | 4/2015 | Ludwin | A61B 34/10 |
| | | | 600/587 |

| | | | |
|---|---|---|---|
| 2016/0183841 A1 | 6/2016 | Duindam et al. |
| 2019/0261945 A1 | 8/2019 | Funka-Lea et al. |
| 2020/0054399 A1 | 2/2020 | Duindam et al. |
| 2020/0359968 A1 | 11/2020 | Hagfors et al. |
| 2020/0390417 A1 | 12/2020 | Gijsbers et al. |
| 2021/0137634 A1 | 5/2021 | Lang |
| 2022/0000537 A1 | 1/2022 | Davies et al. |
| 2022/0287779 A1 | 9/2022 | Poland et al. |

OTHER PUBLICATIONS

Jurgen Biermann, Christoph Bode, Stefan Asbach, "Intracardiac Echocardiography during Catheter-Based Ablation of Atrial Fibrillation", Cardiology Research and Practice, vol. 2012, Article ID 921746, 8 pages, 2012.

Zh E Luo et al: "Magnetic Navigation for Thoracic Aortic Stentgraft Deployment Using Ultrasound Image Guidance", IEEE Transactions on Biomedical Engineering, IEEE, USA, vol. 60, No. 3, Mar. 1, 2013.

* cited by examiner

SAFETY ALERT BASED ON 4D INTRACARDIAC ECHO (ICE) CATHETER TRACKING

CROSS-REFERENCE TO RELATED APPLICATIONS

This application is a continuation of Nonprovisional U.S. application Ser. No. 17/901,325 filed Sep. 1, 2022, which is hereby incorporated by reference in its entirety for any and all purposes.

FIELD OF THE DISCLOSURE

The present disclosure relates generally to treatment systems utilizing intra-body medical probes, and particularly to using a location-tracked medical ultrasound (US) probe to alert of potential hazard from a location-tracked treatment probe.

BACKGROUND OF THE DISCLOSURE

Various methods for guiding a catheter using a medical ultrasound probe have been proposed. For example, U.S. Pat. No. 7,981,038 describes a method and a system for producing images of a subject, such as the heart of a human being. The method may comprise acquiring ultrasound images of the subject with a catheter comprising a position sensor. The method may also comprise capturing a plurality of 4D surface registration points in the acquired ultrasound images corresponding to points on the subject. The method may also comprise registering, in space and time, a high-resolution 4D model of the subject with the plurality of 4D surface registration points. The method may also comprise displaying high resolution, real-time images of the subject during a medical procedure based on the registration of the high resolution 4D model to the 4D surface registration points. Examples of the present disclosure are especially useful in left atrium ablation procedures. According to other embodiments, two or more catheters could be used. In such examples, the clinician could insert a second catheter into the relevant area of the heart where the second catheter includes the ablation device. Preferably, such an ablation catheter would also include a position sensor so that a position tracking system could track the position and orientation of the second catheter. That way, the clinician could use one catheter for acquiring the ultrasound images and the other catheter to perform the ablation.

The present disclosure will be more fully understood from the following detailed description of the examples thereof, taken together with the drawings in which:

DETAILED DESCRIPTION OF EXAMPLES

Overview

Figure 1:
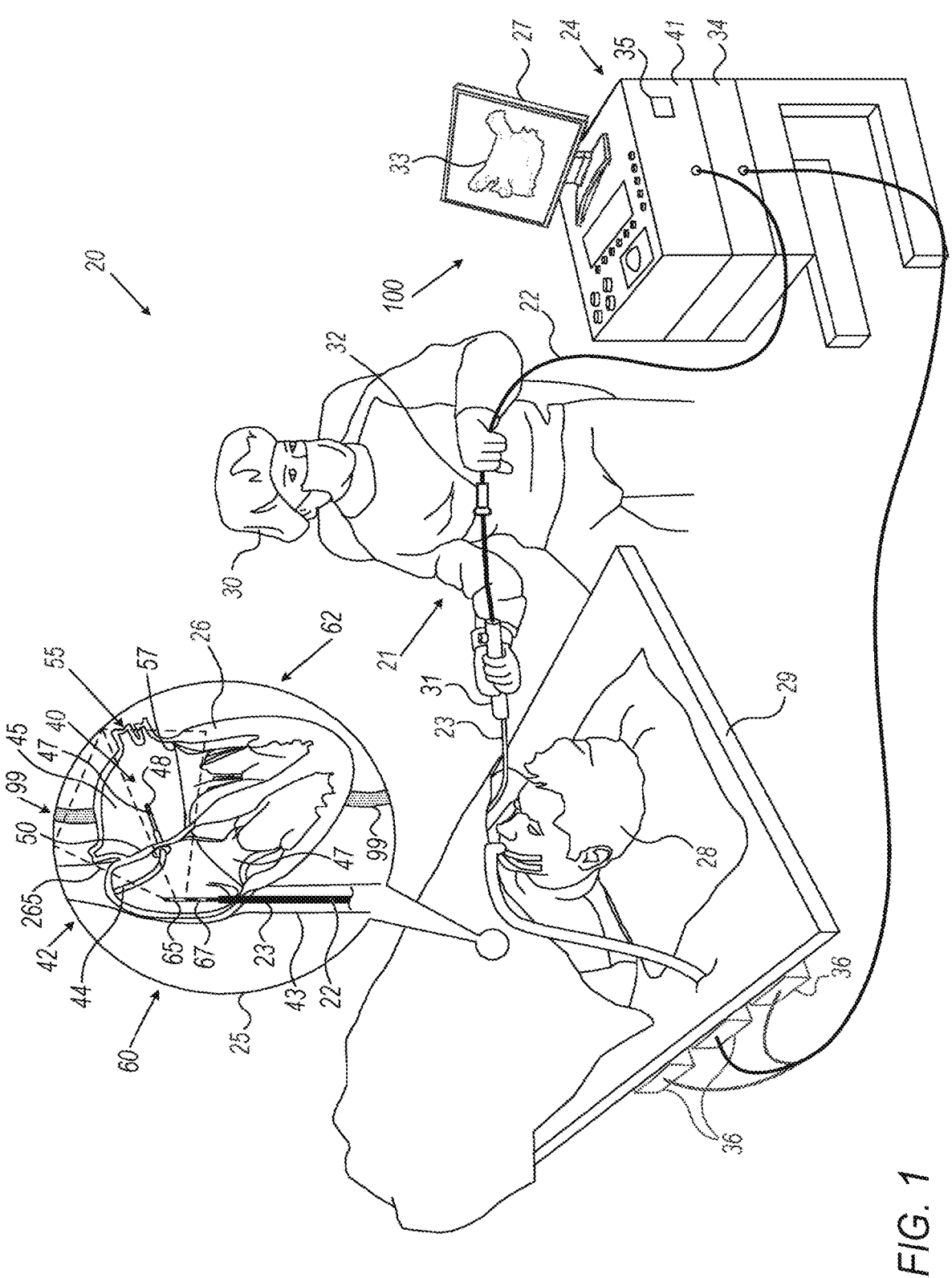
FIG. 1 is a schematic, pictorial illustration of an ultrasound imaging-based system that can alert in real-time a user performing an ablation when the ablation catheter is too proximate to a sensitive region, in accordance with an example of the present disclosure.

When using a probe to perform an invasive treatment of an internal organ, such as a surgical cut or an ablation, there may be specific areas of the organ that a physician may want to avoid. As an example, when forming a cardiac transeptal puncture, it is important to avoid puncturing the aorta. When radiofrequency (RF) ablating an ostium of a pulmonary vein it is important to avoid forming a lesion through the esophagus wall.

If ultrasound imaging is available, e.g., intracardiac echography (ICE), the physician may scan the surrounding area of a target treatment site to search for sensitive tissue regions (also called hereinafter "landmark locations") and make a mental note of such specific landmarks that should be avoided prior to selecting a location for performing the treatment (e.g., puncture or ablation). During the invasive procedure, the system may display one or more selected ultrasound image slices captured in real-time by an ICE probe so that the physician can verify the safety of the invasive procedure.

However, sensitive tissue areas to be avoided may not appear in selected ultrasound image slices displayed to the physician during the procedure. Sensitive tissue areas may also move during the procedure. Moreover, increasing the number of ultrasound image slices displayed may not be practical and may not help the user understand the real-time updated 3D information.

Examples of the present disclosure that are described herein provide methods and systems for alerting the physician if a treatment device fitted on a treatment probe is placed at specific areas that the physician may want to avoid. In some examples, the physician scans the volume with a 4D ICE ultrasound probe prior to ablating or puncturing. The physician uses a graphical user interface (GUI) to tag (e.g., delineate with one click) on the images landmark locations to be avoided. Once landmarks are tagged, the 4D ultrasound acquisition of the tagged tissue regions in images continues, without necessarily showing images of the tagged regions to the physician. A software module uses the real-time ultrasound data to track the locations of the landmarks in real-time.

To this end, the disclosed technique uses a 4D ICE probe which images in real-time the treatment device fitted on a treatment probe. Both the 4D ICE probe and the treatment probe are position-tracked by a position-tracking system, using position senors (e.g., magnetic sensors) fitted to the probes. The sensor outputs first signals indicative of first positions of the ultrasound transducer array inside the organ. As the position sensor in the 4D ICE probe is preregistered with the 2D ultrasound array of the 4D ICE probe, the positions of imaged voxels of the anatomical structure are also known.

The 2D array of the 4D ICE probe produces a sector-shaped ultrasound beam having a wide field of view (FOV), and is thus able to image large anatomical structures of the organ, such as an entire cardiac chamber. The wide FOV of the ultrasound beam enables the US probe to acquire the various sensitive tissue regions, even those not currently displayed to the physician. In other words, the US probe is able to capture all the relevant landmarks while the invasive procedure is undertaken, including landmarks that are not currently displayed to the physician.

As noted above, the location of the treatment device is also known, for example based on an accurate integral position senor (e.g., a magnetic sensor) fitted to the treatment probe, where the senor outputs second signals indicative of second positions of the treatment device inside the organ. To relate the positions of the two different probes, a processor of the position-tracking system registers the positions of the US probe and the treatment probe with one another. The processor further compares in real time the tracked locations of landmarks with a tracked location of the invasive treatment probe tip (e.g., of an electrode of an ablating catheter or of a surgical cutting/piercing tool, such as a transeptal needle). This way, the processor can relate in real-time the location of the treatment device to that of tagged landmark locations to an accuracy of 1 mm. Based on such capability, the processor warns the physician if the treatment probe tip is too near the tagged tissue region.

Therefore, in some examples, a medical system is provided that comprises a 4D ultrasound probe, a treatment probe, and a processor. The processor is configured to (i) receive tagging on ultrasound images acquired using the 4D ultrasound probe of one or more tissue regions of the organ, (ii) register the positions of integral position sensors of the ultrasound imaging and treatment probe one with the other, (iii) using the registered positions, track a position of the treatment device fitted to the treatment probe relative to the one or more tagged tissue regions, and (iv) alert a user in real-time when the treatment device is within a predefined proximity to a tagged tissue region.

The user may set thresholds for defining the proximity to the tagged tissue region (e.g., to a tagged landmark location) required before providing a warning to the user. The warning may be visual, audial and/or haptic. This warning serves as a safety net for the physician. Even if the landmark location is not in the FOV of the real-time image slice being displayed on the screen, the system still identifies the proximity and provides the warning.

System Description

FIG. 1 is a schematic, pictorial illustration of an ultrasound (US) imaging-based system 20 that can alert in real-time a user performing an ablation when the ablation catheter is too proximate to sensitive tissue region, in accordance with an example of the present disclosure. System 20 uses a 4D ultrasound probe 21 with an US probe distal end assembly 60 (shown in an inset 25) comprising a 2D ultrasound array 65 and am integral position sensor 67, to monitor in real-time a location-tracked radiofrequency (RF) ablation catheter 40 having a catheter distal end assembly 62 comprising a position sensor 47 and an ablation electrode 48.

Physician 30 advances distal end assembly 60 of US probe 21 into the right atrium of heart 26 via the inferior vena cava (IVC) 43. Form therein, physician images septum wall 50 between atria (typically before performing a transeptal puncture). In the shown example, ablation catheter 40 is inserted via superior vena cava (SVC) 42 using a sheath 44.

As seen, the 2D ultrasound-array 65 array produces a 3D sector-shaped ultrasound beam 265 occupying a defined solid angle; (such a beam is referred to herein as a "wedge 265"). With the wide FOV covered by wedge 265, the 2D ultrasound-array is able to image a substantial volume of an organ, such as an entire cardiac chamber (e.g., the entire left atrium (LA) 45).

Distal end assembly 60 is fitted at the distal end of a shaft 22 of the catheter. Shaft 22 is inserted through a sheath 23 into a heart 26 of a patient 28 lying on a surgical table 29. The proximal end of shaft 22 is connected to a control console 24. To direct the ultrasound array into a required orientation, the physician can, for example, use a manipulator 32 near the proximal end of US probe 21.

Integral position sensor 67 of US probe 21 is preregistered with array 65 of the US probe. Because of the integral location sensor, the spatial coordinates of every voxel in the imaged cardiac chamber are known. Specifically, sensor 67 is configured to output first signals indicative of the location and orientation of the ultrasound transducer array 65 inside heart 26.

Any imaged target anatomical structure (e.g., left atrium 45, including ostia 55 of pulmonary veins) can be presented to physician 30 by processor 41 on a monitor 27, e.g., as a volume rendering 33.

Subsequently to puncturing septum wall 50 (e.g., using sheath 44), US probe 21 images the entire LA 45 while ablation catheter 40 is placed therein, for example, in vicinity of an ostium 55. The 2D ultrasound-array produced images therefore include the ablation electrode 48.

Therefore, further seen is distal end assembly 62 of RF ablation catheter 40, inserted via sheath 44 into LA 45 to perform an ablation therein using electrode 48 while being imaged in real-time with the 4D ICE probe 21. As illustrated, esophagus 99 passes in proximity of a posterior wall of LA 45, and the sensitive esophagus 99 tissue may suffer thermal damage if exposed to ablation heat.

To alert proximity of the RF ablation electrode 48 location to sensitive tissue regions (e.g., of esophagus 99), the user or the processor tag sensitive regions, such as portion of the posterior wall overlapping esophagus 99. The physician uses a graphical user interface (GUI) 100 to tag on ultrasound image or rendering (e.g., delineate with one click) the landmark locations to be avoided. To this end, the physician scans the volume with the 4D ICE ultrasound probe prior to ablating or puncturing. GUI 100 may include a touchscreen 27, as well as a keyboard and a track ball.

Once tagged, e.g., by the physician, the ultrasound acquisition of the tagged tissue regions continues, without necessary showing the tagged regions to the physician. A software module uses the real-time ultrasound data to track the locations of the landmark in real-time. Using the software, a processor further compares the tracked locations of landmarks with a real time location of the invasive probe tip (e.g., of an ablating catheter or a transeptal needle) and warns the physician if the RF probe tip electrode 48 is too near the tagged tissue region. The system alerts the physician if ablation electrode 48 is brought too near to an unrelated tissue region that can be harmed by an RF ablation.

Control console 24 comprises a processor 41, typically a general-purpose computer, with suitable front end and interface circuits 38 for receiving signals from catheter 21. Console 24 also comprises a driver circuit 34 configured to drive magnetic field generators 36. During the navigation of distal end 22 in heart 26, console 24 receives location and orientation signals from position sensors 67 and 47 in response to magnetic fields from external field generators 36. Magnetic field generators 36 are placed at known positions external to patient 28, e.g., below table 29 upon which the patient is lying. These location and orientation signals are indicative of the location and orientation of ultrasound-array 65 in a coordinate system of the position tracking system.

The method of location and orientation sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

Processor 41 is programmed in software to carry out the functions described herein. The software may be downloaded to a memory 35 of the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, including in FIG. 2, that enables processor 41 to perform the disclosed steps, as further described below.

The example configuration shown in FIG. 1 is chosen purely for the sake of conceptual clarity. The disclosed techniques may similarly be applied using probe/catheter access other than through IVC 43/SVC 44, such as via another vein or via an artery. While in the example described above the alert is against hazard to esophagus 99, any sensitive anatomical structure may be tagged to avoid being damaged, such as the left atrium appendage (LAA) 57 and ridge regions in vicinity of septum 50.

Real-Time Monitoring of a Position-Tacked Treatment Catheter Using Position-Tacked 4D Ice Probe As noted above, to track the locations of the landmark in real-time using 4D ultrasound data, the processor runs a software module. In the process, the processor further compares the tracked locations of landmarks with a real time location of the invasive probe tip (e.g., of an electrode of ablating catheter or a transeptal needle). The processor warns the physician if the probe tip is too near the tagged tissue region. This alert can be provided without displaying a relevant image to the physician. Nevertheless, in some examples, it is beneficial that the physician will receive a relevant view (e.g., a 2D or 3D reconstruction) that images the cause of the alert.

Figure 2:
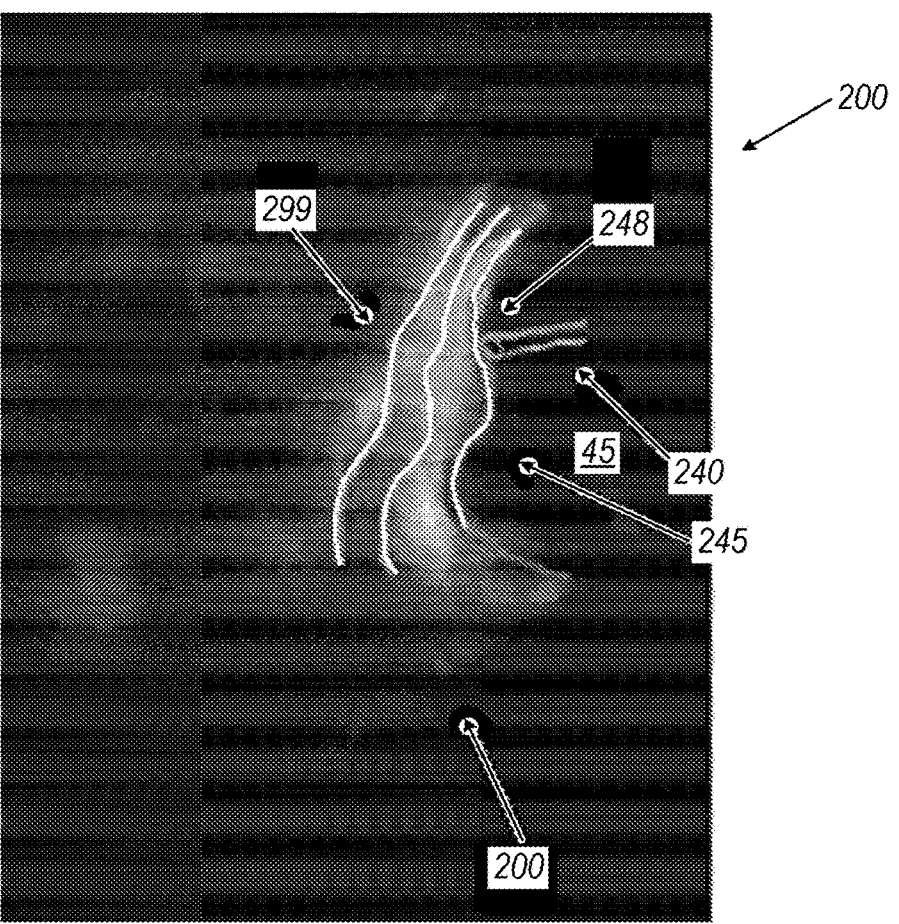
FIG. 2 is a schematic, pictorial illustration of an ultrasound image that the system of FIG. 1 generates in real time to visualize the cause of the alert, in accordance with an example of the present disclosure.

FIG. 2 is a schematic, pictorial illustration of an ultrasound image 200 that system 20 of FIG. 1 generates in real time to visualize the cause of the alert, in accordance with an example of the present disclosure. While the shown image in FIG. 2 is that of a slice, in general the image can be a 3D rendering.

FIG. 2 was generated and presented by processor 41 following the processor issuing an alert (e.g., an audiovisual alert). Image 200 (e.g., ultrasound view 200) highlights an ablation electrode 248 of a catheter 240 being in contact with a tagged region 245 of the posterior wall of LA 45, thereby being too proximate to a delineated esophagus region 299. (As determined using a distal sensor of probe 240, sensor not shown in FIG. 2 but shown in FIG. 1 as sensor 47). As seen, the physician receives a view that illustrates the why the system issued an alert, with the displayed view clearly showing the spatial relation between the aforementioned elements in proximity (i.e., ablation electrode relative to esophagus).

The user may instruct the processor to generate other views, for example, from a different direction of view of the treatment device relative to the tagged tissue region, or a 3D rendering.

Figure 3:
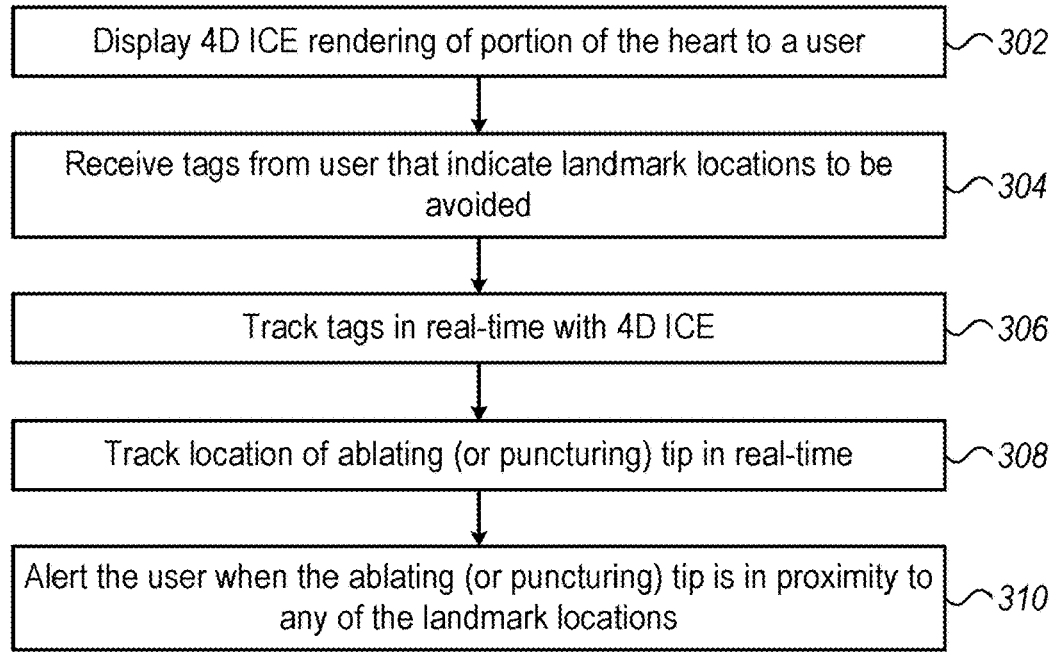
FIG. 3 is a flow chart that schematically describes a method of alerting in real-time a physician performing treatment when a treatment probe is too proximate to a tagged tissue region, in accordance with an example of the present disclosure.

A Method of Real-Time Monitoring of a Position-Tacked Treatment Catheter Using Position-Tacked 4D Ice Probe FIG. 3 is a flow chart that schematically describes a method of alerting in real-time a physician performing treatment when a treatment probe is too proximate to a tagged tissue region, in accordance with an example of the present disclosure. By way of example, the system referred to is system 20 of FIG. 1 with the treatment probe being ablation catheter 40. The algorithm, according to the presented example, carries out a process that begins with physician 30 imaging heart 26, as seen in FIG. 1, at an ICE step 302. Processor 41 displays a 3D rendering of the imaged portion of the heart.

At a tagging step 304, processor 41 receives (e.g., from physician 30) tags that indicate landmark location (one or more tissue regions, such as within a posterior wall of LA 45) to be avoided during RF ablation.

Next, at a tracking step 306, while the physician places ablation catheter 40 to have electrode 48 at the required position for ablation, processor 41 uses the 4D ICE and a software to track the tags in real-time. The tagging benefits the wide FOV of wedge 265, where even tagged tissue regions that are currently not displayed to physician 30 are still acquired with US probe 21, and the acquisition data is processed to enable the tracking.

In parallel, at a treatment device tracking step 308, processor 41 uses magnetic tracking system to track position electrode 48 while the physician places ablation catheter 40 to begin ablation. As the tracking system has the US probe tracking signals (from sensor 67) and these from sensor 47 of catheter 40 registered, processor 41 can related in real-time the location of electrode 48 to the that of landmark locations and within a 1 mm accuracy.

Finally, at an alerting step 310, processor 41 issue an alert (e.g., a blinking message accompanied with a sound blip) whenever the processor identifies that location of electrode 48 and one of the of landmark locations are closer to one to the other than a predefined minimal distance. For example, the processor alerts if the electrode is in contact with the posterior wall of LA 45 just anteriorly to esophagus 99.

The example flow chart shown in FIG. 3 is chosen purely for the sake of conceptual clarity. For example, additional steps, such as occasional X-ray imaging may be performed.

Although the examples described herein mainly address the monitoring of a cardiac treatment probe with a cardiac ultrasound imaging probe, the technique described herein can also be used in other organs, such as of the gastro system.

EXAMPLES

Example 1

A medical system (20) includes an ultrasound probe (21), a treatment probe (40, 240), and a processor (41). The ultrasound probe is configured for insertion into an organ of a body and includes an ultrasound transducer array (65) configured to image a volume of the organ, and a first sensor (67) configured to output first signals indicative of first positions of the ultrasound transducer array inside the organ.

The treatment probe is configured for insertion into the organ, and includes a treatment device (48, 248) fitted at a distal end of the treatment probe, and a second sensor (47) configured to output second signals indicative of second positions of the treatment device inside the organ. The processor is configured to (i) receive tags, which have been added by a user to one or more ultrasound images (200) acquired using the ultrasound probe mark one or more tissue regions (245) of the organ, (ii) register the first positions of the ultrasound transducer array and the second positions of the treatment device with one another, (iii) using the registered first positions and second positions, track a relative position between the treatment device and the one or more tagged tissue regions, and (iv) alert a user in when the treatment device (248) is within a predefined proximity to a tagged tissue region (245).

Example 2

The system (20) according to example 1, wherein the first and second sensors are magnetic position sensors configured to generate the first and second signals in response to a magnetic field applied by a position tracking system.

Example 3

The system according to any of examples 1 and 2, wherein the processor (41) is configured to alert the user by issuing an audio-visual alert.

Example 4

The system according to any of examples 1 through 3, wherein the processor (41) is configured to generate an ultrasound view (200) showing the treatment device relative to the tagged tissue region.

Example 5

The system according to any of examples 1 through 4, wherein the processor (41) is configured to generate an ultrasound view (200) having a Field Of View (FOV) that does not contain a tagged tissue region, and to alert the user when the treatment device is within the predefined proximity to the tagged tissue region even though the tagged tissue region is not visible in the ultrasound view.

Example 6

The system according to any of examples 1 through 5, wherein the treatment device comprises one of a surgical cutting tool, a transseptal access device, and an ablation electrode (48, 248).

Example 7

The system according to any of examples 1 through 6, wherein the processor (41) is configured to receive the tags by the user tagging the ultrasound images using a graphical user interface (GUI) (100).

Example 8

The system according to any of examples 1 through 7, wherein the processor (41) is configured to receive the tags by receiving a tagged anatomical map, which is registered with an ultrasound image, and using the tagged anatomical map to tag the ultrasound image.

Example 9

The system according to any of examples 1 through 8, wherein the organ is a heart (26).

Example 10

A method includes inserting an ultrasound probe into an organ of a body, the ultrasound probe including: an ultrasound transducer array configured to image a volume of the organ, and a first sensor configured to output first signals indicative of first positions of the ultrasound transducer array inside the organ. A treatment probe is inserted into the organ, the treatment probe including a treatment device fitted at a distal end of the treatment probe, and a second sensor configured to output second signals indicative of second positions of the treatment device inside the organ. Tags are received, which have been added by a user to one or more ultrasound images acquired using the ultrasound probe and mark one or more tissue regions of the organ. The first positions of the ultrasound transducer array and the second positions of the treatment device are registered with one another. Using the registered first positions and second positions, a relative position is tracked, between the treatment device and the one or more tagged tissue regions. A user is alerted when the treatment device is within a predefined proximity to a tagged tissue region.

It will thus be appreciated that the examples described above are cited by way of example, and that the present disclosure is not limited to what has been particularly shown and described herein above. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
    an ultrasound probe comprising:
        an ultrasound transducer array configured to image a volume of an organ; and
        a first sensor configured to output one or more first signals indicative of one or more first positions of the ultrasound transducer array inside the organ;
    a treatment probe comprising:
        a treatment device fitted at a distal end of the treatment probe; and
        a second sensor configured to output one or more second signals indicative of one or more second positions of the treatment device inside the organ; and
    a processor, which is configured to:
        receive one or more tags indicative of a position on one or more ultrasound images acquired using the ultrasound probe, wherein the one or more tags mark one or more tissue regions of the organ;

register the first positions of the ultrasound transducer array and the second positions of the treatment device with one another;

using the registered first positions and second positions, track a relative position between the treatment device and the one or more tagged tissue regions; and generate an ultrasound view having a Field Of View (FOV) that does not contain a tagged tissue region.

2. The system according to claim 1, wherein the processor is further configured to alert a user when the treatment device is within a predefined proximity to a tagged tissue region.

3. The system according to claim 2, wherein the processor is configured to alert the user by issuing an audio-visual alert.

4. The system according to claim 1, wherein the processor is configured to alert a user when the treatment device is within a predefined proximity to the tagged tissue region even though the tagged tissue region is not visible in the ultrasound view.

5. The system according to claim 1, wherein the first and second sensors are magnetic position sensors configured to generate the first and second signals in response to a magnetic field applied by a position tracking system.

6. The system according to claim 1, wherein the processor is configured to generate an ultrasound view showing the treatment device relative to the tagged tissue region.

7. The system according to claim 1, wherein the treatment device comprises one of a surgical cutting tool, a transseptal access devices, and an ablation electrode.

8. The system according to claim 1, wherein the processor is configured to receive the tags by a user tagging the ultrasound images using a graphical user interface (GUI).

9. The system according to claim 1, wherein the processor is configured to receive the tags by receiving a tagged anatomical map, which is registered with an ultrasound image, and using the tagged anatomical map to tag the ultrasound image.

10. The system according to claim 1, wherein the organ is a heart.

11. A method, comprising:

inserting an ultrasound probe into an organ of a body, the ultrasound probe comprising:

an ultrasound transducer array configured to image a volume of the organ; and a first sensor configured to output one or more first signals indicative of one or more first positions of the ultrasound transducer array inside the organ;

inserting a treatment probe into the organ, the treatment probe comprising:

a treatment device fitted at a distal end of the treatment probe; and a second sensor configured to output one or more second signals indicative of one or more second positions of the treatment device inside the organ;

receiving one or more tags indicative of a position on one or more ultrasound images acquired using the ultrasound probe, wherein the one or more tags mark one or more tissue regions of the organ;

registering the first positions of the ultrasound transducer array and the second positions of the treatment device with one another;

using the registered first positions and second positions, tracking a relative position between the treatment device and the one or more tagged tissue regions; and generating an ultrasound view having a Field Of View (FOV) that does not contain a tagged tissue region.

12. The method according to claim 11, further comprising alerting a user when the treatment device is within a predefined proximity to a tagged tissue region.

13. The method according to claim 12, wherein the alerting the user comprises issuing an audio-visual alert.

14. The method according to claim 11, further comprising alerting a user when the treatment device is within a predefined proximity to the tagged tissue region even though the tagged tissue region is not visible in the ultrasound view.

15. The method according to claim 11, wherein the first and second sensors are magnetic position sensors configured to generate the first and second signals in response to a magnetic field applied by a position tracking system.

16. The method according to claim 11, wherein generating an ultrasound view comprises showing the treatment device relative to the tagged tissue region.

17. The method according to claim 11, wherein the treatment device comprises one of a surgical cutting tool, a transseptal access device, and an ablation electrode.

18. The method according to claim 11, wherein receiving the tags comprises a user tagging the ultrasound images using a graphical user interface (GUI).

19. The method according to claim 11, wherein receiving the tags comprises receiving a tagged anatomical map, which is registered with an ultrasound image, and using the tagged anatomical map to tag the ultrasound image.

20. A system, comprising:

an ultrasound probe comprising:

an ultrasound transducer array configured to image a volume of an organ; and a first sensor configured to output one or more first signals indicative of one or more first positions of the ultrasound transducer array inside the organ;

a treatment probe comprising:

a treatment device fitted at a distal end of the treatment probe; and a second sensor configured to output one or more second signals indicative of one or more second positions of the treatment device inside the organ; and a processor, which is configured to:

receive, via a graphical user interface (GUI), one or more tags indicative of a position on one or more ultrasound images acquired using the ultrasound probe, wherein the one or more tags mark one or more tissue regions of the organ;

register the first positions of the ultrasound transducer array and the second positions of the treatment device with one another;

using the registered first positions and second positions, track a relative position between the treatment device and the one or more tagged tissue regions; and alert a user when the treatment device is within a predefined proximity to a tagged tissue region.

* * * * *